Figure 4:
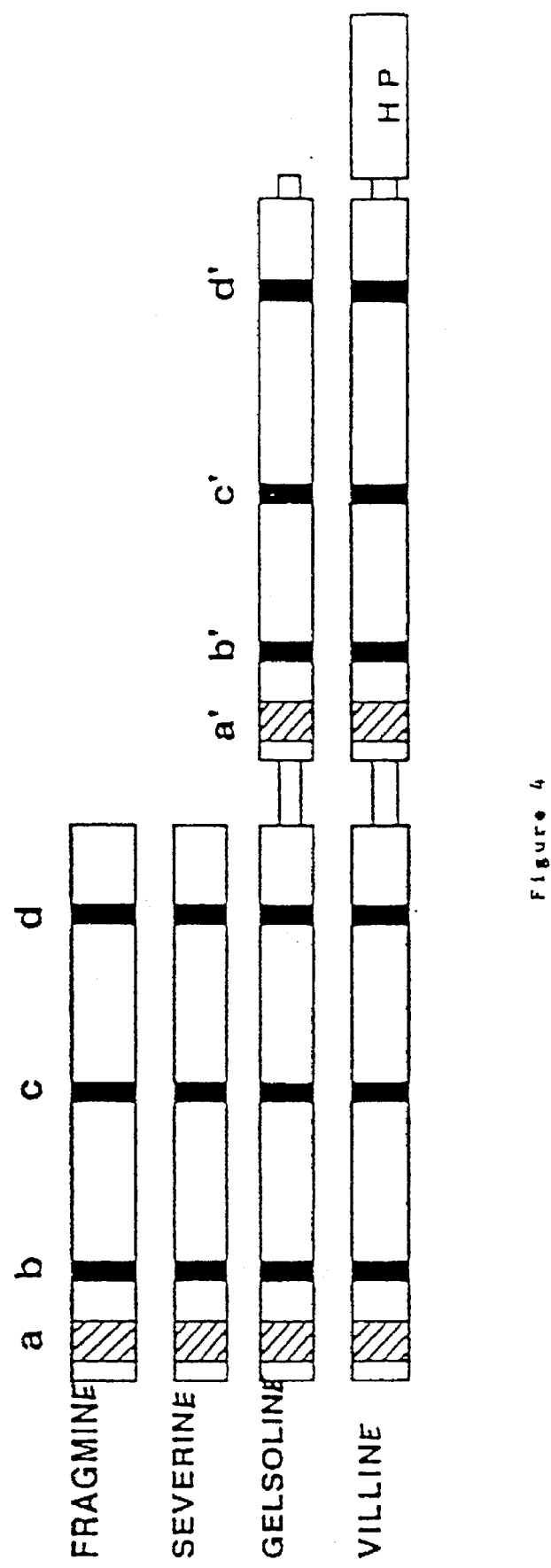

United States Patent [19]
Arpin et al.

[11] Patent Number: 5,652,101
[45] Date of Patent: Jul. 29, 1997

[54] SPECIFIC NUCLEIC ACID FRAGMENTS OF THE GENE FOR HUMAN VILLIN-THEIR USE FOR DIAGNOSTIC PURPOSES

[75] Inventors: Monique Arpin; Eric Pringault; Alphonse Garcia, all of Paris; Daniel Louvard, Sceaux, all of France

[73] Assignee: Institut Pasteur, Paris, France

[21] Appl. No.: 355,224

[22] Filed: Dec. 9, 1994

Related U.S. Application Data

[63] Continuation of Ser. No. 978,468, Nov. 19, 1992, abandoned, which is a continuation of Ser. No. 814,047, Dec. 26, 1991, which is a continuation of Ser. No. 427,824, Oct. 27, 1989.

[30] Foreign Application Priority Data

Oct. 28, 1988 [FR] France ................... 88 14208

[51] Int. Cl.$^6$ .............. C07H 21/04; C12Q 1/68
[52] U.S. Cl. .............. 435/6; 435/320.1; 536/23.1; 536/23.2; 536/24.31
[58] Field of Search ............... 536/23.1, 23.2, 536/24.31; 435/320.1, 6

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,188,967 | 2/1993 | Louvard et al. | 436/501 |

FOREIGN PATENT DOCUMENTS

| | | |
|---|---|---|
| 0186271 | 7/1986 | European Pat. Off. |
| 0206849 | 12/1986 | European Pat. Off. |

OTHER PUBLICATIONS

Pringault et al. EMBO Journal 5(12): 3119–3124, 1986.
Bazari et al. P.N.A.S. 85: 4986–4990, 1988.
Arpin et al., J. of Cell Biol., vol. 107, Nov. 1988, pp. 1759–1766.
E. Pringault et al.; "A human villin cDNA clone to investigate the differentiation of intestinal and kidney cells in vivo and in culture," The EMBO Journal, vol. 5, No. 12 (1986), pp. 3119–3124.
W.L. Bazari et al.; "Villin sequence and peptide map identify six homologous domains"; Proceedings of the National Academy of Sciences of the United States of America, vol. 85, Jul. 1988, pp. 4986–4990.
E. Andre et al.; "Severin, gelsolin, and villin share a homologous sequence in regions presumed to contain F-actin severing domains"; The Journal of Biological Chemistry, vol. 263, No. 2, (Jan. 15, 1988); pp. 722–727.
S. Robine et al.; "Can villin be used to identify malignant and undifferentiated normal digestive epithelial cells?"; Proceedings of the National Academy of Sciences of the United States of America; vol. 82, (Dec., 1985), pp. 8488–8492.
M. Arpin et al.; "Sequence of human villin in large duplicated domain homologous with other actin-severing proteins and a unique small carboxy-terminal domain related to villin specificity," Journal of Cell Biology, (USA), vol. 107, (Nov. 1988), pp. 1759–1766.
W.L. Bazari et al.; "Villin cDNA Sequence Correlates With Functional Domain," The Journal of Cell Biology, (USA), vol. 105, p. 112a, No. 623 (1988).
M.F. Rousseau-Merck et al.; "Localization of the villin gene on human chromosome 2q35–q36 and on mouse chromosome 1," Human Genetics (1988) 78:130–133.

*Primary Examiner*—Stephanie W. Zitomer
*Assistant Examiner*—Paul B. Tran
*Attorney, Agent, or Firm*—Finnegan, Henderson, Farabow, Garrett & Dunner, L.L.P.

[57] ABSTRACT

The invention relates to nucleic acid fragments characterized in that they comprise from 8 to 40 nucleotides and in that their sequence is contained either in the DNA coding sequence of the gene for human villin or in any DNA fragment exactly complementary to one of the former and hence containing the same number of deoxynucleotides, or any corresponding RNA fragment containing the same number of ribonucleotides. The invention also relates to the application of these fragments to a procedure for the in vitro detection of the presence of a nucleic acid characteristic of human villin.

25 Claims, 6 Drawing Sheets

```
1CATTCTCCCCCAGGCTCACTCACCATGACCAAGCTGAGCCCCCAAGTCAAAGGCTCTCTCAACATCACCACCCCGGGGC
TGCAGATATGGAGGATCGAGGCCATGCAGATCAGTGTGCCTGTTCCTTCCAGCACCTTTCTTCGATGGTCACTGC
TACATCATCCTGGCTATCCACACAGACAGCCAGCAGCCTGCTTCCTATGACTTCCTCCACTACTGGATTGGCCAGGACTCATCCCT
GGATGACCAGGGGGCAGCTGCCATCTACACCACACAGATGATGACTTCCTGAAGGCCGGGCTGTGCAGCACCGCGAGG
TCCAGGGCAACGAGAGCGAGCCTTCCGAGGCTACTTCAAGCAAGGCCTTGTGATCCGGCAAAGGGGCGTGGCTTCTGGC
ATGAAGCACGTGGAGACCAACTCCTATGACGTCCAGAGGTGCTGCATGTCAAGGGCAAGAGGAACGTGGTAGCTGGAGA
GGTAGAGATGTCCTGGAAGAGTTTCAACCAGGGGATGTTTCCTCCTGGACCTTGGGAAGCTTATCATCCAGTGGAATG
GACCGGAAAGCACCCGTATGGAGAGACTCAGGGCATGACTCTGGCCAAGGAGATCCGAGACCAGGAGGCGGGGAGGGCGC
ACCTATGTAGGCGTGGTGGACGGAGAATGAATTGGCATCCCCGAAGCTGATGGAGTGATGAACCACGTGCTGGCGAA
GCGCAGGGAGCTGAAGGCGGCCGTGCCCGACACGGTGGAGGGAAGTCGCCACAGGACCTGCACTCAAGGCTGCACTCAAACTGTACCATGTGT
CTGACTCCGAGGGGAATCTGGTGGTGAGGGAAGTCGCCACACGGAAGTCTGGAAAGGGAAGAAAGCCAATGAGCAGGAGAAGGAGCCAT
TACATCCTGACCAGGGGGCCTGAAGATCTACGTGTGAGAAAGGAAGAAGCCAATGAGCAGGAGAAGATGATGGGCTGAGT
GAGCCATGCCTGAACTTCATCAAAGCCAAGCAGTACCCACCAAGCACACAGGTGCAGAATGATGGGCTGAGT
CGGCCGTCTTTCAGCAGCTCTTCCAGAAGTGGACAGCCTCCAACCGGACCTCAGGCCTAGGCAAAACCCACACTGTGGC
TCCGTGGCCAAAGTGGAACAGGTGAAGTTCCATGCCACATCCATGCCATGTCAAGCCTCAGGTGGCTGCCCAGCAGAGAT
GGTAGATGATGGGAGTGGGCGACTGCTACCTGTGCGTCTACACCTCATCGGCGAGAAGCAGCATTACCTGCTCTACGTT
GCCACTTCTATGGGGCGACTGCTACCTGTGCGTCTACACCTCATCGGCGAGAAGCAGCATTACCTGCTCTACGTT
TGGCAGGGCAGCCAGCCAAGATGAAATTACAGCATCAGCTTATCAAGCCGTCATCCTGGACCAGAGTACAATGG
TGAACCAGTCCAGATCCGGGTCCCGAACTAACAACTTGGAGACAACTTGGAGACGGGGCCCTGTTCCAGGTCCAGGGAACTGGCGCC
AACAACACCAAGGCCTTTGAGGTCCCAGCCGGCGGGGCCAATTTCGTCGTCAATTCCAATGATGTCTCTTTGTCCTCAAGACCCAGTC
TTGCTGCTATCTATGGTGTGGGAAGGGTTGTAGCGGGACGAGCGGGAGATGGCCAAGATGTTGCTGACACCATCTCCC
GGACGGAGAAGCAAGTGGTGTGGAAGGGCAGGAGCCAGCCAACTTCTGGATGGCCTGGGTGGGAAGGCCCCCTATGCC
AACACCAAGAGACTACAGGAAGAAAAACCTGGTCATCACCCCGGCTCTTTGAGTGTTCCAACAAGACTGGGCGCTTCCT
GGCCAGATCACTGCTGAGGTCGACTTCAATCAGGATGACTTGGAAGAGAAGGCCGCAGCAACCACTGCACAGAATACCTCAAGACCCAT
TCTTCTGGATTGGGAAACATGCCAACGAGGAGGAAGAGAAGGCCGCAGCAACCACTGCACAGAATACCTCAAGACCCAT
CCCAGCGGCGTGACCCTGAGACCCCCATCATTGTGGTGAACAGGACACGAGCCCCCACCTTCACAGGCTGGTTCCT
GGCTTGGGATCCCTTCAAGTGGAGTAACACAAATCCTATGAGGACCTGAAGGCGAGTCTGGCAACCTTAGGGACTGGA
GCCAGATCACTGCTGAGGTCACAAGCTGTTCAATGCTAACAGCCCCAAAGTGACGTGTTCAATGCTAACAGCTAACAGCCCCAGCAGGAGAACA
ATCTTCCCCCTGAGACTAGTAGTGAACAGCCTTTGGGATGACTCCAGCTGCTTCTGCCTCGATGGAAGCAACAAA
CCTGTCCATTGAAGATTTCACTCAGGCCTATTGGAGAAGACTATTTTGAGAAGAGTAGTCGTGGTTGTAAAGCAGTACCCTGATTGTAGGGTCTC
ACCTCAAGAAAAGAAAAAAGGACTATTTTGAGAAGAGTAGTCGTGGTTGTAAAGCAGTACCCTGATTGTAGGGTCTC
ATTTCTCACCGATATTAGTCCTACACCATTGAAGTGAAATTTTGCAGATGCCTATGAGCACAAACTTCTGTGCAA
ATGCCCAGTTTGTTTAATAATGTACCTATTCCTTCAGAAAGATGATACCCCCAAAAAAAAAA
```

Figure 1

```
                                            -1   •   •   •   •   •   •   •   •   •   •   •   •
                                        MET THR LYS LEU SER ALA GLN VAL LYS GLY SER LEU ASN ILE THR THR PRO
            CATTCTCCCCCAGGCTCACTCACC ATG ACC AAG CTG ACC GCC CAA GTC AAA GGC TCT CTC AAC ATC ACC ACC CCG  75

GLY LEU GLN ILE TRP ARG ILE GLU ALA MET GLN MET VAL PRO VAL PRO SER SER THR PHE GLY SER PHE PHE ASP
GGG CTG CAG ATA TGG AGG ATC GAG CCC ATG CAG ATG GTG CCT GTT CCT TCC AGC ACC TTT GGA AGC TTC TTC GAT  150

GLY ASP CYS TYR ILE ILE LEU ALA ILE HIS LYS THR ALA SER SER LEU SER TYR ASP ILE HIS TYR TRP ILE GLY
GGT GAC TGC TAC ATC ATC CTG GCT ATC CAC AAG ACA CCC ACC AGC CTG TCC TAT GAC ATC CAC TAC TGG ATT GGG  225

GLN ASP SER SER LEU ASP GLU GLN GLY ALA ALA ALA ILE TYR THR THR GLN MET ASP ASP PHE LEU LYS GLY ARG
CAG GAC TCA TCC CTG GAT GAG CAG GGG GCA GCT GCC ATC TAC ACC ACA CAG ATG GAT GAC TTC CTG AAG GGC CGG  300
                                100
ALA VAL GLY HIS ARG GLU VAL GLN GLY ASN GLU SER GLU ALA PHE ARG GLY TYR PHE LYS GLN GLY LEU VAL ILE
GCT GTG CAG CAC CGC GAG GTC CAG GGC AAC GAG AGC GAG GCC TTC CGA GGC TAC TTC AAG CAA GGC CTT GTG ATC  375

ARG LYS GLY GLY VAL ALA SER GLY MET LYS HIS VAL GLU THR ASN SER TYR ASP VAL GLN ARG LEU LEU HIS VAL
CGG AAA GGG GGC GTG GCT TCT GGC ATG AAG CAC GTG GAC ACC AAC TCC TAT GAC GTC CAG AGG CTG CTG CAT GTC  450

LYS GLY LYS ARG ASN VAL VAL ALA GLY GLU VAL GLU MET SER TRP LYS SER PHE ASP ARG GLY ASP VAL PHE LEU
AAG GGC AAG AGG AAC GTG GTA GCT GGA GAG GTA GAG ATG TCC TGG AAG AGT TTC AAC CGA GGG GAT GTT TTC CTC  525

LEU ASP LEU GLY LYS LEU ILE ILE GLN TRP ASN GLY PRO GLU SER THR ARG MET GLU ARG LEU ARG GLY MET THR
CTG GAC CTT GGG AAG CTT ATC ATC CAG TGG AAT GGA CCG GAA AGC ACC CGT ATG GAG AGA CTC AGG GGC ATG ACT  600

LEU ALA LYS GLU ILE ARG ASP GLN GLU ARG GLY GLY ARG THR TYR VAL GLY VAL VAL ASP GLY GLU ASN GLU LEU
CTG GCC AAG GAG ATC CGA GAC CAG GAG CGG GGA GGG CGC ACC TAT GTA GGC GTG GTG GAC GGA GAG AAT GAA TTC  675

ALA SER PRO LYS LEU MET GLU VAL MET ASN HIS VAL LEU GLY LYS ARG ARG GLU LEU LYS ALA ALA VAL PRO ASP
GCA TCC CCG AAG CTG ATG GAG GTG ATG AAC CAC GTG CTG GGC AAG CGC AGG GAG CTG AAG GCG GCC GTG CCC GAC  750

THR VAL VAL GLU PRO ALA LEU LYS ALA ALA LEU LYS LEU TYR HIS VAL SER ASP SER GLU GLY ASN LEU VAL VAL
ACG GTG GTG GAG CCG GCA CTC AAG GCT GCA CTC AAA CTG TAC CAT GTG TCT GAC TCC GAG GGG AAT CTG GTG GTG  825

ARG GLU VAL ALA THR ARG PRO LEU THR GLN ASP LEU LEU SER HIS GLU ASP CYS TYR ILE LEU ASP GLN GLY GLY
AGG GAA CTC GCC ACA CGG CCA CTG ACA CAG GAC CTG CTC AGT CAC GAG GAC TGT TAC ATC CTG GAC CAG GGG GGC  900
                                300
LEU LYS ILE TYR VAL TRP LYS GLY LYS LYS ALA ASN GLU GLN GLU LYS LYS GLY ALA MET SER HIS ALA LEU ASN
CTG AAG ATC TAC GTG TGG AAA GGG AAG AAA CCC AAT GAG CAG GAG AAG AAG GGA GCC ATG AGC CAT GCG CTG AAC  975

PHE ILE LYS ALA LYS GLN TYR PRO PRO SER THR GLN VAL GLU VAL GLN ASN ASP GLY ALA GLU SER ALA VAL PHE
TTC ATC AAA CGG AAG CAG TAC CCA CCA AGC ACA CAG GTG GAG GTG CAG AAT GAT GGG GCT GAG TCG CCC CTC TTT  1050

GLN GLN LEU PHE GLN LYS TRP THR ALA SER ASN ARG THR SER GLY LEU GLY LYS THR HIS THR VAL GLY SER VAL
CAG CAG CTC TTG CAG AAG TGG ACA GCG TCC AAC CGG ACC TCA GGC CTA GGC AAA ACC CAC ACT GTG GGC TCC GTG  1125

ALA LYS VAL GLU GLN VAL LYS PHE ASP ALA THR SER MET HIS VAL LYS PRO GLN VAL ALA ALA GLN GLN LYS MET
GCC AAA GTC GAA OAG GTG AAG TTC CAT GCC ACA TCC ATG CAT GTC AAG CCT CAG GTG CCT GCC CAG CAG AAG ATG  1200
                                400
VAL ASP ASP GLY SER GLY GLU VAL GLN VAL TRP ARG ILE GLU ASN LEU GLU LEU VAL PRO VAL ASP SER LYS TRP
GTA GAT CAT GGG AGT GGG GAA GTG CAC GTC TGG CCC ATT GAG AAC CTA GAG CTC GTA CCT GTG GAT TCC AAG TGG  1275

LEU GLY HIS PHE TYR GLY GLY ASP CYS TYR LEU LEU LEU TYR THR TYR LEU ILE GLY GLU LYS GLN HIS TYR LEU
CTA GGC CAC TTC TAT GGG GGC GAC TGC TAC CTG CTG CTC TAC ACC TAC CTC ATC GGC GAG AAG CAG CAT TAC CTG  1350

LEU TYR VAL TRP GLN GLY SER GLN ALA SER GLN ASP GLU ILE THR ALA SER ALA TYR GLN ALA VAL ILE LEU ASP
CTC TAC GTT TGG CAG GGC AGC CAG GCC AGC CAA GAT GAA ATT ACA GCA TCA GCT TAT CAA GCC GTC ATC CTG GAC  1425
```

Figure 2A

```
GLN LYS TYR ASN GLY GLU PRO VAL GLN ILE ARG VAL PRO MET GLY LYS GLU PRO PRO HIS LEU MET SER ILE PHE
CAG AAG TAC AAT GCT GAA CCA GTC CAG ATC CGG GTC CCA ATG GGC AAG GAG CCA CCT CAT CTT ATG TCC ATC TTC  1500
                                 500
LYS GLY ARG MET VAL VAL TYR GLN GLY GLY THR SER ARG THR ASN ASN LEU GLU THR GLY PRO SER THR ARG LEU
AAG GGA CGC ATG GTG GTC TAC CAG GGA GGC ACC TCC CGA ACT AAC AAC TTG GAG ACC GGG CCC TCC ACA CGG CTG  1575

PHE GLN VAL GLN GLY THR GLY ALA ASN ASN THR LYS ALA PHE GLU VAL PRO ALA ARG ALA ASN PHE LEU ASN SER
TTC CAG GTC CAG GGA ACT GGC GCC AAC AAC ACC AAG GCC TTT GAG GTC CCA GCG CGC GCC AAT TTC CTC AAT TCC  1650

ASN ASP VAL PHE VAL LEU LYS THR GLN SER CYS CYS TYR LEU TRP CYS GLY LYS GLY CYS SER GLY ASP GLU ARG
AAT GAT GTC TTT GTC CTC AAG ACC CAG TCT TGC TGC TAT CTA TGG TGT GGG AAG GGT TGT AGC GGG GAC CAG CGG  1725

GLU MET ALA LYS HET VAL ALA ASP THR ILE SER ARG THR GLU LYS GLN VAL VAL VAL GLU GLY HIS GLU PRO ALA
GAC ATG GCC AAG ATG GTT GCT GAC ACC ATC TCC CGG ACG GAG AAG CAA GTG GTG GTG GAA GGG CAC GAG CCA GCC  1800
                                 600
ASN PHE TRP MET ALA LEU GLY GLY LYS ALA PRO TYR ALA ASN THR LYS ARG LEU GLN GLU GLU ASN LEU VAL ILE
AAC TTC TGG ATG GCC CTG GGT GGG AAG GCC CCC TAT GCC AAC ACC AAG AGA CTA CAG GAA GAA AAC CTG GTC ATC  1875

THR PRO ARG LEU PHE GLU CYS SER ASN LYS THR GLY ARG PHE LEU ALA THR GLU ILE PRO ASP PHE ASN GLN ASP
ACC CCC CGG CTC TTT GAG TGT TCC AAC AAG ACT GGG CGC TTC CTG GCC ACA GAG ATC CCT GAC TTG AAT CAG CAT  1950

ASP LEU GLU GLU ASP ASP VAL PHE LEU LEU ASP VAL TRP ASP GLN VAL PHE PHE TRP ILE GLY LYS HIS ALA ASN
GAC TTG GAA GAG GAT GAT GTG TTC CTA CTA GAT GTG TGG GAC CAG GTC TTC TTC TGG ATT GGG AAA CAT GCC AAC  2025

GLU GLU GLU LYS LYS ALA ALA ALA THR THR ALA GLN GLU TYR LEU LYS THR HIS PRO SER GLY ARG ASP PRO GLU
GAC GAG GAG AAG AAG GCC GCA GCA ACC ACT GCA CAG GAA TAC CTC AAG ACC CAT CCC AGC GGG CGT GAC CCT GAG  2100
                                 700
THR PRO ILE ILE VAL VAL LYS GLN GLY HIS GLU PRO PRO THR PHE THR GLY TRP PHE LEU ALA TRP ASP PRO PHE
ACC CCC ATC ATT GTG GTG AAG CAG GGA CAC GAG CCC CCC ACC TTC ACA GGC TGG TTC CTG GCT TGG GAT CCC TTC  2175

LYS TRP SER ASN THR LYS SER TYR GLU ASP LEU LYS ALA GLU SER GLY ASN LEU ARG ASP TRP SER GLN ILE THR
AAG TGG AGT AAC ACC AAA TCC TAT GAG GAC CTG AAG GCG GAG TCT GGC AAC CTT AGG GAC TGG AGC CAG ATC ACT  2250

ALA GLU VAL THR SER PRO LYS VAL ASP VAL PHE ASN ALA ASN SER ASN LEU SER SER GLY PRO LEU PRO ILE PHE
GCT GAG GTC ACA AGC CCC AAA GTG GAC GTG TTC AAT GCT AAC AGC AAC CTC AGT TCT GGG CCT CTG CCC ATC TTC  2325

PRO LEU GLU GLN LEU VAL ASN LYS PRO VAL GLU GLU LEU PRO GLU GLY VAL ASP PRO SER ARG LYS GLU GLU HIS
CCC CTG GAG CAG CTA GTG AAC AAG CCT GTA GAG GAG CTC CCC GAG GGT GTG GAC CCC AGC AGG AAG GAG GAA CAC  2400
                                 800
LEU SER ILE GLU ASP PHE THR GLN ALA PHE GLY MET THR PRO ALA ALA PHE SER ALA LEU PRO ARG TRP LYS GLN
CTG TCC ATT GAA GAT TTC ACT CAG GCC TTT GGG ATG ACT CCA CCT GCC TTC TCT GCT CTG CCT CGA TGG AAG CAA  2475
                                 826
GLN ASN LEU LYS LYS GLU LYS GLY LEU PHE  *
CAA AAC CTC AAG AAA GAA AAA GGA CTA TTT TGAGAAGAGTAGCTGTGGTTGTAAAGCAGTACCCTACCCTGATTGTAGGGTCTCATTTT  2564
CTCACCGATATTAGTCCTACACCAATTGAAGTGAAATTTTGCAGATGTGCCTATGAGCACAAACTTCTGTGGCAAATGCCAGTTTTGTTTAATAATGTA  2663
CCTATTCCTTCAGAAAGATGATACCCCAAAAAAAAAAAA 2703
```

Figure 2B

```
                                                             TKLSAQVKGS
                                                             - -   -
MAPHRPAPALLCALSLALCALSLPVRAATASRGASQAGAPQGRVPEARPNSMVVEHPEFL
         10        20        30        40        50

20        30        40        50        60
LNITTPGLQIWRIEAMQMVPVPSSTFGSFFDGDCYIILAIHKTASSLS-YDIHYWIGQDS
:::::::-:  - -:::--   :  ::  ::  :-::          ::-:::-:---
KAGKEPGLQIWRVEKFDLVPVPTNLYGDFFTGDAYVILKTVQLRNGNLQYDLHYWLGNEC
         70        80        90       100       110

70        80        90       100       110       120
SLDEQGAAAIYTTQMDDFLKGRAVQHREVQGNESEAFRGYFKQGLVIRKGGVASGMKHVE
: ::-:::::  :  :-::  :  :::::::::::: ::   :  :::::-:: -:::::::-:::
SQDESGAAAIFTVQLDDYLNGRAVQHREVQGFESATFLGYFKSGLKYKKGGVASGFKHVV
        130       140       150       160       170

130       140       150       160       170       180
TNSYDVQRLLHVKGKRNVVAGEVEMSWKSFNRGDVFLLDLGKLIIQWNGPESTRMERLRG
:    ::::- :::-: : : :: -:: ::: :: :-:::: : ::-: :-: :::--
PNEVVVQRLFQVKGRRVVRATEVPVSWESFNNGDCFILDLGNNIHQWCGSNSHRYERLKA
        190       200       210       220       230

190       200       210       220       230       240
MTLAKEIRDQERGGRTYVGVVDGEHELASPKLMEVHHHVLGKRRELKAAVPDTVVEPALK
-- :  :::-:: ::  : :  -  -:-   -        :::  -  : :-  ::   : :
TQVSKGIRDNERSGRARVHVSEEGTEPEAMLQ------VLGPKPALPAGTEDTAKEDAAN
        250       260       270       280       290

250       260       270       280       290       300
AAL-KLYHVSDSEGNLVVREVATRPLTQDLLSH-EDCYILDQGGL-KIYVWKGKKANEQE
: :::  ::    :-- :  ::      -       ::: ::: :    :: ::::: ::   :
RKLAKLYKVSNGAGTMSVSLVADEMPFAQGALKSEDCFILDHGKDGKIFVWKGKQANTEE
        300       310       320       330       340       350

310       320       330       340       350       360
KKGAMSHALNFIKAKQYPPSTQVEVQNDGAESAVFQQLFQKWTASNRTSGLGKTHTVGSV
-:-:-   :  ::     ::  -::: :  -:-:-  -: :-: :       : :::  -       -
RKAALKTASDFITKMDYPKQTQVSVLPEGGETPLFKQFFKNWRDPDQTDGLGLSYLSSHI
        360       370       380       390       400       410

370       380       390       400       410       420
AKVEQVKFDATSHHVKPQVAAQQKMVDDGSGEVQVWRIENLELVPVDSKWLGHFYGGDCY
:  :: : :::  --:       -:::  :  :::-:   :-:::::     ::::       : :::::-:
ANVERVPFDAATLHTSTAMAAQHGMDDDGTGQKQIWRIEGSNKVPVDPATYGQFYGGDSY
        420       430       440       450       460       470

430       440       450       460       470       480
LLLYTYLIGEKQHYLLYVWQGSQASQDEITASAYQAVILDQKYNGEPVQIRVPMGKEPPH
--::-:   : -:   --: :::  : -:::- :::       ::        : ::: ::- :::: :
IILYNYRHGGRQGQIIYNWQGAQSTQDEVAASAILTAQLDEELGGTPVQSRVVQGKEPAH
        480       490       500       510       520       530

490       500       510       520       530       540
LMSIFKGRMVVYQ-GGTSRTNNLETGPSTRLFQVQGTGANNTKAFEVPARANFLNSNDVF
:::-: :----   :::::       :::::::: -- :  :-:-::- -:  ::::: :
LMSLFGGKPMIIYKGGTSREGGQTAPASTRLFQVRANSAGATRAVEVLPKAGALNSNDAF
        540       550       560       570       580       590

550       560       570       580       590       600
VLKTQSCCYLWCGKGCSGDEREMAKMVADTISRTEKQVVVEGQEPAWFWHALGGKAPYAH
::::  :   ::: : : :  :-  :  -   -  -   ::  ::-::  ::  ::::::: :  -
VLKTPSAAYLWVGTGASEAEKTGAQELLRVLRAQPVQVA-EGSEPDGFWEALGGKAAYRT
        600       610       620       630       640       650
```

Figure 3A

```
          610       620       630       640       650       660
TKRLQEENLVIT-PRLFECSNKTGRFLATEIPDFNQD-DLEEDDVFLLDVWDQVFFWIGK
 - ::  - -     ::::  ::::  :::-   :-:         ::   :::-:::  :::::-:-::
SPRLKDKKMDAHPPRLFACSNKIGRFVIEEVPGELMQEDLATDDVMLLDTWDQVFVWVGK
         660       670       680       690       700       710

670       680       690       700       710       720
HANEEEKKAAATTAQEYLKTHPSGRDPETPIIVVKQGHEPPTFTGWFLAWDPFKWSNTKS
 -::::     :  :-:     :- :   :     ::    :::  :::::  :::-:  ::::-::    ::
DSQEEEKTEALTSAKRYIETDPANRDRRTPITVVKQGFEPPSFVGWFLGWDDDYWSVDPL
         720       730       740       750       760       770

730       740       750       760       770       780
YEDLKAESGNLRDWSQITAEVTSPKVDVFNANSNLSSGPLPIFPLEQLVNKPVEELPEGV
  -
DRAMAELAA
  780
          790       800       810       820
DPSRKEEHLSIEDFTQAFGMTPAAFSALPRWKQQNLKKEKGLF
```

Figure 3B

SPECIFIC NUCLEIC ACID FRAGMENTS OF THE GENE FOR HUMAN VILLIN-THEIR USE FOR DIAGNOSTIC PURPOSES

This application is a continuation, of application Ser. No. 07/978,468, filed Nov. 19, 1992, abandoned which is a continuation of application Ser. No. 07/814,047, filed Dec. 26, 1991, which is a continuation of application Ser. No. 07/427,824, filed Oct. 27, 1989.

The invention relates to nucleic acid fragments, the sequence of which is specific for the gene for human villin.

By "sequence specific for the gene of human villin" is meant any sequence contained in the coding sequence of this gene, any sequence contained in the messenger RNA resulting from the transcription of the said coding sequence, and also a sequence complementary to those just mentioned.

The invention also relates to the use of these nucleic acid fragments to detect the expression of the gene for human villin. This application of the nucleic acid fragments of the invention makes it possible, among other things, to detect in vitro the presence of tumor cells derived from primary tumors of the gastric or intestinal region or from metastases, in a biological sample (tissue or biological fluid) taken from organs of a patient other than those of the digestive or intestinal sphere. Another application of these fragments consists in the detection of the polymorphism of the restriction fragments of the human genome.

Studies performed up to the present have recorded the significance of villin as marker of metastases in tissues other than those of the digestive or intestinal region. In this respect the European patent application No. 0206849 filed on 30 Apr. 1986 describes agents for the detection of villin in a biological sample taken from an organ other than those of the digestive or intestinal sphere. The patent application EP0206849 takes advantage of the fact that villin is generally present, more particularly in the brush borders observed at the surface of the enterocytes, at the apex of the elongated cells present at the surface of the internal wall of the intestine and in the cells of the proximal tubule of the kidney. On the other hand, villin is not detected in other organs such as the lungs, the brain etc. . . . When metastases of digestive or intestinal tumors occur, cells producing villin may migrate to different organs. Villin may then be detected in these metastases and the diagnosis of a primary tumor of digestive or intestinal origin may be made.

The diagnostic agents described in the above-mentioned application EP 0206849 and intended for the detection of the protein of its messenger or of the gene coding for it are constituted either by antibodies directed against villin or by all or part of a DNA corresponding to the complete mRNA of human villin or also by a fragment of cDNA containing at least a part of the nucleotide sequence coding for the amino acids of the COOH extremity of human villin.

Up to the present only this COOH terminal part of the nucleic acid of villin had been sequenced.

Generally speaking, villin belongs to the class of proteins having an activity for binding to actin. Villin exhibits a specificity which is characteristic of it within the group of proteins capable of binding to actin. This specificity relates, on the one hand, to its double function in vitro depending on the calcium concentration of the medium and, on the other hand, to its very specific tissue distribution. Nonetheless, in certain regions of its amino acid sequence, villin shows certain sequence homologies with another protein present in higher eucaryotes, gelsolin.

In particular, the comparison of the amino acid sequences of these proteins shows that they possess a similar overall structural organisation, with the exception of the COOH terminal part, comprising a duplicated domain of four segments, three of which are homologous. Thus, in the part which is common, villin and gelsolin exhibit an overall homology of about 50% of their amino acids, this homology being stronger at certain regions. It is essentially in the particular COOH terminal part designated as "head-piece" (terminal region) that villin differs from gelsolin.

The invention follows from the discovery after sequencing of the regions coding for villin that, contrary to all expectation, the identity of organisation of villin and gelsolin and the homology of their amino acid sequences had no equivalents at the level of the nucleic acids coding, respectively, for villin and gelsolin.

The inventors have taken advantage of these observations in order to develop new means to detect in a specific manner the expression of the gene coding for human villin. These means make possible in particular the early detection of the presence of messenger RNA (mRNA) resulting from the transcription of the gene for human villin.

The means in conformity with the invention for detecting the expression of the gene coding for human villin are constituted by nucleic acid fragments specific for the coding sequence of the gene for human villin or for the transcription of this gene.

The result of the observation made by the inventors is that a nucleic acid fragment containing at least 8 nucleotides and derived from the DNA coding for human villin or from the messenger RNA transcribed from this coding DNA can be specific for the gene for human villin and, in particular is distinct from corresponding fragments of the DNA coding for gelsolin.

The invention thus relates to any nucleic acid fragment comprising a sequence of 8 to 40, and preferably 20 to 40 nucleotides, characterized in that its sequence is contained in the sequence of the DNA coding for the gene for human villin represented in FIG. I. It also relates to any DNA fragment exactly complementary to one of those just mentioned and hence containing the same number of deoxyribonucleotides as well as any corresponding RNA fragment containing the same number of ribonucleotides.

The invention relates in particular to any nucleic acid fragment characterized in that it comprises 8 to 40 nucleotides and that its sequence is contained in the part external to the "Head piece" of the DNA or RNA specific for the gene for human villin, as defined above.

The invention relates more particularly to the sequences defined above in a single stranded form but also,in the case of the DNAs,in a double stranded form.

The fragments previously defined can be isolated by cleavage and, where necessary trimmed by a suitable enzyme, for example Bal 31, starting from the gene coding for human villin or from cDNA prepared from the mRNA resulting from the transcription of this gene. These fragments can also be synthesized by chemical or enzymatic means on the basis of the sequence given in FIG. I which represents the sequence coding for the gene of human villin.

The chemical synthesis of one of the fragments may be carried out by implementing the "phosphodiester" method, the steps of which are summarized below:

The 5'-phosphate end of one of the nucleotides, after protection of the functional groups, reacts (condensation reaction) with the 3'-hydroxyl end of another equally protected nucleoside or nucleotide by using dicyclohexylcarbodiimide or an arylsulfonyl chloride. The chain of nucleotides is thus lengthened by the implementation of similar condensation steps.

Protecting groups for the nucleotide functions may, for example, consist of a monomethoxytrityl (MMTr) group, an acetyl (Ac) group or an anisoyl (An) group.

Chemical synthesis can also be carried out by the "phosphotriester" method which makes it possible to block each internucleotide phosphodiester function as the synthesis of the sequence progresses.

In order to carry out this method, a totally protected mononucleotide is used containing a blocked 3'-phosphotriester group.

A third method leading to the chemical synthesis of a nucleic acid fragment is the "phosphite-triester" method. Preferably, this method is used in conjunction with an insoluble support to which the 3' end of the oligonucleotide to be synthesized is attached. This immobilization of the nucleotide by coupling dispenses with the purification steps after each cycle of condensation. In order to carry out this method the appropriate mononucleotides, bloked beforehand, are added sequentially and the reagents and undesired starting materials are removed by filtration.

The protecting groups of the nucleic acid synthesized are removed at the end of the reaction, the nucleic acid is then cleaved from the support and purified by electrophoresis or HPLC.

When the oligonucleotide synthesized is bound to a support of the polymeric type in a column, the filtration steps may be replaced by washing.

The methods of chemical synthesis described can benefit from the teaching of chapter 2 "Isolation, Identification and Characterisation of DNA fragments" of the monograph entitled "From Genes to clones" by E. L. WINNACKER.

It is understood that any region of the coding sequence or of the corresponding mRNA may serve as a starting point for obtaining a nucleic acid fragment of the invention identical with or complementary to these sequences provided that the specificity of the sequence of the nucleotides of the fragment with respect to the coding DNA or the mRNA of villin is respected.

The invention also relates to the special application consisting of the utilization of the defined nucleic acid fragments for the constitution of nucleotide primers (also designated as primers), capable of inducing, under defined conditions, the initiation of the synthesis of all or part of a nucleic acid specific for the gene for villin.

By primer is meant a sequence of nucleotides (oligonucleotide) advantageously constituted by a nucleic acid fragment defined above, in particular any fragment advantageously comprising from 8 to 40 nucleotides and preferably from 20 to 40 nucleotides and exhibiting the following properties:

depending on its nature, it is capable of hybridizing specifically with a complementary corresponding sequence of either the DNA coding for the gene for villin or the mRNA corresponding to this gene, or of a sequence which is complementary to them, it is capable of inducing the synthesis of a nucleic acid complementary to that to which it hybridizes (this latter is then called the matrix) in a buffered solution and under conditions of pH and temperature suitable for this synthesis, in the presence of an inducing agent for the synthesis, in particular a polymerase or a reverse transcriptase and in the presence of suitable nucleotides. The synthetic product obtained starting from the fragment serving as primer is called the elongation product of the primer.

Buffered solutions and conditions of pH and temperature suitable for the production of the "elongation product of the primer" can be determined by reference to the teaching of the following patents: U.S. Pat. No. 4,683,202 and U.S. Pat. No. 4,683,195, the content of which is incorporated into the present application.

The primer is available in a double stranded or single stranded form. The latter form is usually more favourable for the required property of hybridization with the nucleic acid so that the synthesis of the elongation product can start with the primer and in contact with the matrix.

The utilization of a double stranded primer, denatured before the hybridization step, can lead to competition between, on the one hand, the rehybridization of the primer with the complementary strand and, on the other, the nucleic acid matrix capable of hybridizing with one of the strands of the primer.

The invention relates more particularly to the application of the primers conform ed to the invention to the initiation of the synthesis of a quantity sufficient to be detected of elongation products of the primer in contact with a nucleic acid coding for human villin, present in the sequence of FIG. I, or starting from a mRNA sequence of transcription of the gene for human villin or from sequences complementary to those just mentioned, present in a biological sample, these sequences then acting as matrices complementary to the said primers.

Such an application makes possible, for example, the detection of a change (mutation, deletion . . . ) in the nucleic acid fragment constituting the elongation product of the primer.

In relation to the foregoing discussion, the invention thus relates to a procedure for detecting in vitro the presence of either a nucleic acid coding for human villin or a mRNA resulting from the transcription of the gene for human villin in a biological sample suspected to contain this mRNA, comprising the following steps:

a/ the placing in contact, in the presence of nucleoside triphosphates and a polymerization inducing agent, of the biological sample suspected to contain the mRNA resulting from transcription of the gene for human villin, previously made accessible to a first primer, under conditions permitting hybridization between these primers and the mRNA presumed to be present, and the polymerization starting from these primers hybridized to the mRNA, of the nucleic acid complementary (cDNA) to the mRNA, in order to produce a duplex formed between the elongation product of the primer, hybridized either with the nucleic acid strand coding for human villin or with the corresponding mRNA when they are present in the biological sample, b/ the denaturation of the duplex obtained in step a/ so as to "separate" the elongation product of the primer from the mRNA to be detected, c/ the placing in contact of the elongation product obtained with a second primer (in the sense which has been given to this expression above) having a sequence of nucleotides (1) not complementary to that of the first primer and (2) complementary to a sequence in the elongation product previously formed, d/ if necessary, the repetition of the steps a/ and b/ and c/ in the presence of the first and second primers used in excess and in the presence of the reagents necessary for the production of new elongation products used, in turn, as matrices for additional syntheses, until a sufficient quantity is obtained to be detected by elongation products of the primers used.

e/ the detection of the presence of the elongation products characteristic of the presence of the DNA or the mRNA of human villin.

Such a procedure maybe used, for example, for the in vitro detection of the presence of tumor cells or tumors, or also of metastases of tumors, provided that they are characterized by the abnormal presence of the mRNA of human villin. As an example, mention may be made of the cells derived from the tumorigenesis of intestinal or renal tissues.

The implementation of the above detection procedure is carried out starting from a biological sample taken from a patient and constituted, for example, by a biopsy, a surgically excised sample, a biological fluid.

According to a particular embodiment of the above procedure, the primer, or the first and second primers as well as the nucleotides, are added at the first step in sufficient amount for several cycles of synthesis of the elongation product(s) to be carried out by implementation of the steps of the procedure defined above in order to obtain a desired degree of amplification of the mRNA initially present in the biological sample.

According to a variant of the embodiment of the procedure, these constituents are incorporated into the reaction mixture throughout the entire performance of the steps of the procedure. The nucleotides introduced in the initial step of the above procedure of detection are constituted of deoxyribonucleotides or of ribo-nucleotides depending whether the primers used are constituted of DNA or RNA. A mixture of the two types of nucleotides may also be used.

The agent inducing polymerization starting from the primer hybridized to the nucleic acid serving as matrix is usually constituted by a DNA polymerase when the synthesis of DNA has to be induced or by a reverse transcriptase for synthesizing DNA starting from a RNA matrix. As examples of the polymerases which can be used, mention should be made of the DNA polymerase of E. coli, the Klenow fragment of this DNA polymerase, the $T_4$ DNA polymerase. This list is not, of course, exhaustive. On the contrary, any system, any enzyme capable of being used as catalyst of polymerization is included in the scope of the invention.

The duplex obtained after polymerization starting from a primer, when the elongation product of the primer and the matrix of synthesis are of different kinds, i.e. when the mRNA is initially present in the biological sample, is a heteroduplex when the elongation product of the DNA primer is the cDNA, complementary to the mRNA.

For more details concerning the technique relating to the detection procedure described above, or for working out variants of this procedure, the person skilled in the art may usefully make reference to the principles described in the patents U.S. Pat. No. 4,683,202 and U.S. Pat. No. 4,683,195.

The implementation of the procedure previously described may result, if required, in the amplification of a specific part of the sequence of the mRNA of transcription of the villin gene. In this case recourse may be had to the use of two primers specifically forming the 5' and 3' ends of the sequence to be amplified.

The size of the sequence to be amplified is chosen in order to make possible the detection of the presence of the mRNA presumed to be present. The polymerization starting from a primer may thus be intentionally limited by any suitable means.

The detection of the elongation products of the primers may be made by the standard techniques of detection. According to one embodiment of the invention, the procedure for the detection of the presence of mRNA is characterized in that the nucleotides incorporated to meet the requirements of carrying out the procedure are radioactively labelled and that the detection of the presence of the mRNA presumed to be present corresponds to the detection of the radioactivity of the elongation products synthesized after elimination of the nucleotides not incorporated during the polymerization starting from primers.

Another application of the fragments conforming to the invention relates to their use for the detection of human genetic polymorphism.

By detection of human genetic polymorphism is meant both the genetic identification of an individual and the detection of certain diseases related to the gene for villin or a genetically related gene. The identification of an individual may comprise the analysis of the restriction fragments containing all or part of the gene for villin.

In the context of this application, the nucleic acid fragments defined previously are used as probes.

These probes are used in a biological sample, for example, a tissue or a fluid prepared so as to be accessible to the said probes.

For the implementation of such probes, reference should be made to the European patent application 0186 271, the content of which is incorporated into the present description.

Other characteristics and advantages of the invention will become apparent in the examples which follow and in the figures:

FIG. 1 presents the DNA sequence coding for the gene for human villin;

FIGS. 2A and 2B contains the coding sequence of FIG. 1 and the amino acid sequence of human villin in exact correspondance, FIGS. 3A and 3B shows the comparison between the coding sequences of villin and gelsolin.

FIG. 4 shows the comparative structures of villin, gelsolin and related proteins present in the lower eucaryotes.

SEQUENCING OF THE cDNA COMPLEMENTARY TO THE mRNA OF HUMAN VILLIN

Construction of a cDNA Bank

The total RNA was isolated from a subclone of a HT-29 cell line (HT29-18-C1; Huet et al., 1987) by the method using guanidine isothiocyanate (Chirgwin et al., 1979) and enriched in polyadenylated RNA (poly $A^+$ RNA) by passage through a column of oligodT cellulose (Aviv and Leder, 1972).

The polyadenylated RNA was fractionated according to size on a 5%–20% sucrose gradient and the fractions containing mRNA of villin were identified by Northern blot analysis using a cRNA (complementary RNA) probe corresponding to the carboxy-terminal part of human villin (Pringault et al., 1986, reference 1).

The cDNA was synthesized starting from 1 µg of polyadenylated RNA in conformity with the method described by Gubler and Hoffmann (1983). After methylation of the cDNA with a methylase EcoR1, EcoR1 linkers were ligated to the blunt ends of the cDNA, digested with EcoR1 and separated on a Ultrogel AcA34 (LKB) column in a TE (20 mM Tris, 1 mM EDTA) buffer. 30 ng of cDNA were ligated to 1 µg of the DNA of a vector λgt10 digested by EcoR1 and the particles were encapsidated in vitro ("in vitro packaging") in order to give a cDNA bank containing $10^6$ independent recombinants.

In order to isolate the 5' part of the cDNA of villin, 3 extensions starting from successive primers were carried out using oligonucleotide sequences complementary to the mRNA of villin. The oligonucleotide probes are underlined in FIG. II. The oligonucleotides were hybridized in accordance with a molecular ratio of 10:1 with 2 µg of poly A⁺ mRNA fractionated according to size. The synthesis of cDNA was then carried out in conformity with the conditions described above. The λgt10 bank was then screened with cRNA probes obtained by in vitro transcription (Melton et al., 1984, reference 2) of the cDNA clones already characterized.

Northern Blot Analysis

The poly A⁺ RNA (1.5 µg) isolated from the HT29-18-C1 cell line was fractionated by electrophoresis on 1% agarose gels in the presence of 1M formaldehyde (Lehrach et al., 1977, reference 3) and transferred to nitrocellulose. The imprints were pre-hybridized at 55° C. for 16 hours in 50% formamide, 4×SSC, 0.05 M $Na_2HPO_4$ at pH 7.4 in 1×Denhardt's solution, 250 µg/ml of denatured salmon sperm DNA and 500 µg/ml of tRNA. The hybridization with a RNA probe labelled with $p^{32}$ ($2 \times 10^6$ c.p.m/ml) was carried out for 24 hours at 55° C. in the same solution in the absence of the tRNA. The imprints were washed twice in 1×SSC, 0.1% SDS, once in 0.2×SSC, 0.1% SDS at 65° C. and, finally, once in 0.1×SSC, 0.1% SDS for 30 min. at 70° C.

Sequence Analysis

Restriction fragments of the cDNA were subcloned into M13mp-18-mp19 derivatives and sequenced by the dideoxy-method of chain termination described by SANGER et al. (1977, reference 4). The data for the sequences of the two strands confirm each other.

Analysis of the Protein Sequence

Human villin has been purified by B. West, L. West and M. Mooseker (Department of Biology, Yale University) from brush border cells isolated from a human (Carboni et al., 1987, reference 5) by methods described by Coleman and Mooseker (1985, reference 6). Before sequencing, 25 µg of villin were subjected to electrophoresis on SDS-10% polyacrylamide gel and electrotransferred onto a glassfibre membrane (Whatman GF/C) coated with poly(4-vinyl-N-methylpyridine). The details relating to this method are given in BAUW et al. (1987, reference 7). The immobilized protein was detected by a dilute fluorescamine stain (1 mg/l of acetone), detached from the membrane and transferred to the reaction chamber of a gas phase protein sequenator, Applied Biosystems 470A, operating according to the directions of the manufacturer.

The initial sequencing leads to the sequence of about 10% of the protein deposited on the gel being determined. It is known that the transfer of the protein is rarely quantitatively high (at most, between 60 and 90%) and that a blockage of the $NH_2$ terminal resulting from an artefact occurs during gel electrophoresis (in most cases more than 50% of the protein is blocked), see Moos et al., 1988, reference 8). That is why the value obtained is not abnormally low and probably reflects the $NH_2$ terminal sequence of the majority of the villin molecules rather than the result of a proteolytic cleavage close to the $NH_2$ terminus of a fraction of the villin molecules, the $NH_2$ terminus of which is blocked.

LITERATURE REFERENCES (1) Pringault, E. et al 1986. A human villin cDNA clone to investigate the differentiation of intestinal and kidney cells in vivo and in culture. EMBO J.5:3119–3124

(2) Melton, D. A. et al 1984. Efficient in vitro synthesis of biologically active RNA and RNA hybridization probes from plasmids containing a bacteriophage SP6 promoter. Nucl. Acids Res. 12:7035–7056.

(3) Lehrach, H. et al 1977. RNA molecular weight determinations by gel electrophoresis under denaturing conditions, a critical reexamination. Biochemistry, 16: 4743–4754.

(4) Sanger, F. et al. 1977. DNA sequencing with chain-terminating inhibitors. Proc. Nat. Acad. Sci. 74:5463–5467.

(5) Carboni, J. M. et alm. 1987. Characterization of intestinal brush border cytoskeletal proteins of normal and neoplastic human epithelial cells: a comparison with the arian brush border. Am. J. Pathol. 129 : 589–600.

(6) Coleman, T. R. et al 1.1985. Effects of actin filament cross-linking and filament length on actin-myosin interaction. J. Cell Biol. 101 : 1850–1857.

(7) Bauw, G. et al. 1987. Alterations in the phenotype of plan cells studied by $NH_2$-terminal amino acid-sequence analysis of proteins electroblotted from two-dimensional gel-separated total extracts. Proc. Natl. Acad. Sci. 84 : 4806–4810.

(8) Moos, M. Jr. et al. 1988. Reproducible high yield sequencing of proteins electrphoretically separated and transferred to an inert support. J. Biol. Chem. 263:6005–6008.

We claim:

1. A purified human villin gene comprising the nucleic acid sequence shown in FIG. 2.

2. The nucleic acid of claim 1, wherein said human villin gene encodes the amino acid sequence of human villin shown in FIG. 2.

3. A vector comprising the nucleic acid of claim 1.

4. The vector of claim 3, wherein said human villin gene encodes the amino acid sequence of human villin shown in FIG. 2.

5. A purified nucleic acid fragment consisting essentially of at least eight consecutive nucleotides of the human villin gene located outside the headpiece region of said gene, wherein said human villin gene located outside the headpiece region comprises the sequence beginning with ATG at position 25 to TTC at position 2175 of FIG. 2, and wherein said fragment is 8 to 40 nucleotides.

6. The nucleic acid fragment of claim 5, wherein said fragment is about 20 to 40 nucleotides.

7. The nucleic acid fragment of claim 5, wherein said nucleic acid fragment is DNA.

8. The nucleic acid fragment of claim 5, wherein said nucleic acid fragment is RNA.

9. The nucleic acid fragment of claim 5, wherein said nucleic acid fragment is single-stranded.

10. A nucleic acid fragment, which is complementary to the nucleic acid fragment of claim 9.

11. The nucleic acid fragment of claim 5 wherein said nucleic acid fragment is double-stranded.

12. A vector comprising the nucleic acid fragment of claim 5.

13. A purified nucleic acid fragment consisting essentially of at least 8 consecutive nucleotides of the human villin gene located outside the headpiece region of said gene, wherein said human villin gene located outside the headpiece region encodes the amino acid sequence from MET at position −1 to PHE at position 716 in FIG. 2, and wherein said fragment is 8 to 40 nucleotides.

14. The nucleic acid fragment of claim 13, wherein said fragment is about 20 to about 40 nucleotides.

15. The nucleic acid fragment of claim 13, wherein said nucleic acid fragment is DNA.

16. The nucleic acid fragment of claim 13, wherein said nucleic acid fragment is RNA.

17. The nucleic acid fragment of claim 13, wherein said nucleic acid fragment is single-stranded.

18. A nucleic acid fragment, which is complementary to the nucleic acid fragment of claim 17.

19. The nucleic acid fragment of claim 13, wherein said nucleic acid fragment is double-stranded.

20. A vector comprising the nucleic acid fragment of claim 13.

21. A purified nucleic acid sequence consisting of part of the sequence of the human villin gene located outside of the headpiece region of said gene, wherein said purified nucleic acid sequence begins with an ATG at position 25 to TTC at position 2175 of FIG. 2.

22. A purified nucleic acid sequence that hybridizes with the purified nucleic acid sequence according to claim 21 at 55° C. in 50% formamide, 4×SSC, 0.05 M $Na_2HP0_4$ at pH 7.4 in 1×Denhardt's solution, 250 µg/ml of denatured salmon sperm DNA, and 500 µg/ml of tRNA.

23. The purified nucleic acid sequence according to claim 22 having the following sequence:

5'-CTG CAG ATA TGG AGG ATC GA- 3'.

24. The purified nucleic acid sequence according to claim 22 having the following sequence:

5'-T ACT CAC AAG ACA-3'.

25. The purified nucleic acid sequence according to claim 22 having the following sequence:

5'-ATC CAG TGG AAT GGA CCG-3'.

* * * * *